United States Patent [19]

Kamb

[11] Patent Number: 5,683,880
[45] Date of Patent: Nov. 4, 1997

[54] LINKAGE ANALYSIS OF GENES WITH DISEASES USING DIFFERENCE SPECTRUM ANALYSIS

[75] Inventor: Alexander Kamb, Salt Lake City, Utah

[73] Assignee: Myriad Genetics, Inc., Salt Lake City, Utah

[21] Appl. No.: 499,708

[22] Filed: Jul. 7, 1995

[51] Int. Cl.$^6$ .............................. C12Q 1/68; C07H 21/04; C12P 19/34
[52] U.S. Cl. ........................... 435/6; 435/91.2; 536/24.3; 536/24.31; 536/24.33
[58] Field of Search ..................... 435/6, 91.2; 536/24.3, 536/24.31, 24.33

[56] References Cited

U.S. PATENT DOCUMENTS 5,364,759  11/1994  Caskey et al. .............................. 435/6

OTHER PUBLICATIONS

LeDuc, C. et al. (1995). "Batched Analysis of Genotypes," PCR–Methods And Applications 4:331–336.
Jeffrey, A.J. (1985). "Hypervariable 'minisatellite' regions in human DNA," Nature 314:67–73.
Nakamura, Y. et al. (1987). "Variable Number of Tandem Repeat (VNTR) Markers for Human Gene Mapping," Science 235:1616–1622.
Saiki, R.K. et al. (1985). "Enzymatic Amplification of β–Globin Genomic Sequences and Restriction Site Analysis for Diagnosis of Sickle Cell Anemia," Science 230:1350–1354.
Hunkapiller, T. et al. (1991). "Large–Scale and Automated DNA Sequence Determination," Science 254:59–67.
Smith, L.M. et al. (1986). "Fluorescence detection in automated DNA sequence analysis," Nature 321:674–679.
Mullis, K.B. and Faloona, F.A. (1987). "Specific Synthesis of DNA in Vitro via a Polymerase–Catalyzed Chain Reaction," Methods in Enzymology 155:335–350.
Saiki, R.K. et al. (1988). "Primer–Directed Enzymatic Amplification of DNA with a Thermostable DNA Polymerase," Science 239: 487–491.
Litt, M. and Luty, J.A. (1989). "A Hypervariable Microsatellite Revealed by In Vitro Amplification of a Dinucleotide Repeat within the Cardiac Muscle Actin Gene," Am. J. Hum. Genet. 44:397–401.
Weber, J.L. and May, P.E. (1989). "Abundant Class of Human DNA Polymorphisms Which Can Be Typed Using the Polymerase Chain Reaction," Am. J. Hum. Genet. 44:388–396.

Botstein, D. et al. (1980). "Construction of a Genetic Linkage Map in Man Using Restriction Fragment Length Polymorphisms," Am. J. Hum. Genet. 32:314–331.

Arnheim et al., "Use of pooled DNA samples to detect linkage disequilibrium of polymorphic restriction fragments and human disease: Studies of the HLA class II loci." Proc. Natl. Acad. Sci. USA 82: 6970–6974 Oct. 1985.

Sheffield et al., "Identification of a Bardet–Biedl syndrome locus on chromosome 3 and evaluation of an efficient approach to homozygosity mapping", Hum. Molec. Genet, 3: 1331–1335. Aug. 1994.

Carmi et al., "Use of a DNA pooling strategy to identify a human obesity syndrome locus on chromosome 15", Hum. Molec. Genet. 4:9–13. Jan. 1995.

Khatib et al., "Determining relative microsatellite allele frequencies in pooled DNA samples", PCR Meth. Appl. 4: 13–18. 1994.

Primary Examiner—Jasemine C. Chambers
Assistant Examiner—Scott D. Priebe
Attorney, Agent, or Firm—Venable, Baetjer, Howard & Civiletti, LLP

[57] ABSTRACT

The present invention is directed to a method for rapidly analyzing whether known genetic markers which are found in various lengths in the population, e.g., those containing $(CA)_n$ repeats, are associated with a disease of interest. The method involves using polymerase chain reactions to amplify the DNA in the marker regions and comparing the amplified DNA lengths seen in the normal population with those seen in an affected population of persons. The method involves a pooling of DNA samples from normal patients to average out the normal marker genotype found in the population and also involves a pooling of DNA from affected individuals to give a summing effect to give a stronger signal. The amplified DNA fragments are labeled with two distinguishable markers such as two different colored fluorescent markers, one used to label the amplified DNA from the normal population and the other to label the amplified DNA from the affected population. The amplified products from the normals and the affecteds are pooled, run on a sequencing gel, and a difference spectrum is calculated. Markers which are not associated with the disease will result in a zero or near zero difference spectrum whereas a marker which is associated with the disease will result in a difference spectrum with marked peaks.

8 Claims, No Drawings

LINKAGE ANALYSIS OF GENES WITH DISEASES USING DIFFERENCE SPECTRUM ANALYSIS

BACKGROUND OF THE INVENTION

Advances in the techniques of molecular biology are leading to the development of massive amounts of data concerning the sequence of the genomes of many organisms including humans. Genes are being sequenced with increasing rapidity once they are located, with plans well underway to sequence completely the complete genomes of several organisms including humans. Once genes associated with a disease are located specifically on a chromosome and fully analyzed by DNA sequencing, it may be possible to correct genetic defects found in these genes by gene therapy techniques. Gene therapy is still in its infancy, but there have been some promising results produced already. A prerequisite for performing gene therapy is the identification and sequence analysis of a gene associated with the disease in question. Locating genes specifically associated with a disease is an extremely complex process. Much of this complexity is a result of the very large size of genomes. The haploid human genome consists of approximately 3 billion nucleotides spread across 23 different chromosomes (24 if the X and Y are considered separately, and 25 if one includes the mitochondrial chromosome). Locating a single gene associated with a specific disease presently can take years of research by large groups of scientists working in concert.

Presently, efforts are well underway to sequence the complete human genome. Hopes are to finish this sequencing within another 10 years. Nevertheless, even if the complete sequence of the human genome is determined, these data alone cannot match a gene with a disease. Such a process must be done by chromosome mapping. Typically, one tries to find large families affected with the disease or affected sib pairs. By studying many markers spread throughout the genome and determining which markers are consistently seen with the disease it is possible to locate a chromosomal region likely to contain the gene of interest. Once the chromosomal region has been narrowed to a relatively small region, e.g., 1–5 million base pairs, sequencing studies may take over, this region of DNA being sequenced to determine normal sequence and comparing this normal sequence to the sequence determined from affected individuals. An alternative to sequencing genomic DNA is to identify candidate genes by strategies which look for transcripts, e.g., screening cDNA libraries or using hybrid selection. If a gene is found which consistently is mutated in affected individuals then it is highly likely that the gene is associated with the disease. Useful sequencing methods for DNA were developed in the 1970s and have become highly automated in the succeeding years. DNA sequencing is no longer the rate limiting step in finding a gene associated with a disease. Instead, the hard step today is to map physically a putative gene to a chromosomal location.

Various techniques have been developed for genetic linkage analysis. Given a set of informative families, genetic markers are essential for linking a disease to a region of a chromosome. Such markers include restriction fragment length polymorphisms (RFLPs) (Botstein, D. et al., *Am. J. Hum. Genet.* 32:314–331 (1980), markers with a variable number of tandem repeats (VNTRs) (Jeffreys, A. et al., *Nature* 314:67–73 (1985); Nakamura et al., *Science* 235:1616–1622 (1987)), and an abundant class of DNA polymorphisms based on short tandem repeats (STRs), especially repeats of CpA (Weber and May, *Am. J. Hum. Genet.* 44:388–396 (1989); Litt et al., *Am. J. Hum. Genet.* 44:397–401 (1989)). These STRs are found in microsatellite DNA. Such markers tend to consist of small repeats, for example $(CA)_n$ where n=10–30. The definition of a genetic marker here is that the genetic marker includes the repeat DNA as well as surrounding unique regions of DNA. Other dinucleotide repeats, trinucleotide repeats, or even larger repeats are seen and can be used. These microsatellite repeat markers are useful because they are scattered across the genome at approximately every 100 kilobases. A useful marker is one which is polymorphic in the total population, e.g., if a $(CA)_n$ marker is used, it is not really useful if 99% of the population has the same number of repeats. A CA marker located near gene A may have 20 CA repeats in it. If 99% of the population all has 20 repeats in the marker it is useless as a marker. Contrarily, if instead 10% of the population has 18 repeats, 5% has 19 repeats, 15% has 20 repeats, 30% has 21 repeats, 30% has 22 repeats, and 10% has 23 repeats, the marker may be quite useful. The marker is heterogeneous with six possible repeats. This marker can be used to study gene A. If in a large family with many affected persons, it is seen that all of the affected persons are homozygous or hemizygous for 23 repeats of the CA whereas the unaffected members are never homozygous for the 23 repeat form of the CA satellite marker, this is very suggestive that gene A (or another gene located relatively nearby) is associated with the disease.

SUMMARY OF THE INVENTION

The present invention which is disclosed will prove useful in increasing the rate at which a specific gene can be matched up with a marker and thus localized to a small region of a chromosome. The technique results in an increase of 1 to 2 orders of magnitude for this process. It uses known microsatellite markers, e.g., those containing dinucleotide repeats of $(CA)_n$. Thousands of such markers are scattered throughout the human genome, each with unique sequence on both sides of the dinucleotide repeats. The invention utilizes a process wherein primers are made complementary to each side of the markers to be studied and a polymerase chain reaction is performed. Two sets of reactions are carried out, one in which the primers are labeled with a fluorescent marker, e.g., blue, and the other in which the primers are labeled with a different fluorescent marker, e.g., red. One color primer is used for PCR for persons affected with the disease (affected), the other marker is used for PCR for a group of persons not affected with the disease (normal). The PCR reactions are carried out on several affected and several normal persons, with the DNA samples being amplified separately or by the pooling of several affected samples and the pooling of several normal samples. Several PCRs using several different sets of primers may all be performed together in a single tube and thereby increase the throughput, but this is not necessary. After completing the PCRs, the amplified DNAs are electrophoresed on a gel to separate them by size. Many samples are run in a single lane at one time. It is this last aspect of the invention which most allows for the increased rapidity in locating genes as compared to earlier methods. It is most convenient to run these on an automated sequencing apparatus such as an ABI 373. The intensities of the blue and red are recorded either as the electrophoresis occurs or following electrophoresis. The blue and red spectra are then compared and one is subtracted from the other after appropriate mobility corrections and scaling factors are applied. If the particular marker of interest is not associated with the disease, then the affected and the normal PCR products contain the same relative amounts of each repeat for the marker. The difference spectrum will approximate a relatively flat line. If, however, the marker is associated with the disease, it is likely one multiple of the dinucleotide will prevail in the affecteds. This will appear as a peak in the difference spectrum. If several markers had been mixed together, when a difference spectrum peak is observed, those markers can be reanalyzed separately. By performing the PCR on DNA from several persons (or other organisms) at one time the signals are averaged and results in an improved signal to noise ratio because the background noise will be averaged out. By not only pooling DNA from many individuals to decrease noise, but also by possibly pooling the primers for markers into a single PCR reaction and especially by pooling many reaction products to be run together on a single lane of a gel, there results a dramatic increase in the rate of correlating a marker with a disease.

DESCRIPTION OF THE INVENTION

The present invention is directed to a method to locate more rapidly the chromosomal location of a gene associated with a disease. In general, the invention combines two techniques to accomplish this increase in speed compared to presently used methods of gene mapping. One technique is to pool DNA from several individuals to average out background noise and thus decrease the possibility of false positive results which could lead one astray. The second technique is to analyze several markers together in single lanes of a gel rather than individually, again leading to more rapid analysis.

More specifically, the method of the present invention comprises: (a) selecting several genetic markers; (b) preparing two sets of primer pairs each set complementary to each genetic marker; (c) purifying normal DNA from a population of normal; (d) purifying mutated DNA from a population of affected persons; (e) performing polymerase chain reactions on said normal DNA and on said mutated DNA using the two sets of primers to produce amplified DNA fragments; (f) pooling the amplified DNA fragments and electrophoresing them on a gel; (g) scanning the amplified DNA fragments to measure a first signal wherein the first signal indicates relative amounts of each size of amplified normal DNA fragment and to measure a second signal wherein the second signal indicates relative amounts of each size of amplified mutated DNA; (h) determining a difference spectrum between the first and second signals; and (i) examining the difference spectrum, wherein a difference spectrum showing a difference of close to zero throughout indicates no association of the markers with the disease and wherein a peak in the difference spectrum indicates a positive association of one or more markers with the disease.

The two sets of primer pairs are prepared such that each end of a genetic marker is complementary to one primer of each primer pair such that each pair of primers will amplify a genetic marker in a polymerase chain reaction. At least one primer of each pair from a first set of primer pairs is labeled with a first marker and at least one primer of each pair from a second set of primer pairs is labeled with a second marker wherein the first marker is distinguishable from the second marker. The primers labeled with the first marker are used in the polymerase chain reactions with the normal DNA and the primers labeled with the second marker are used in the reactions with the mutated DNA. The difference spectrum is determined by normalizing the first signal with the second signal to produce a scaled first signal and a scaled second signal and subtracting the scaled first signal from the scaled second signal. The normal DNA is preferably pooled prior to amplification. The affected persons are preferably blood relatives.

A common method of gene mapping as presently performed can be outlined as follows: several gene markers which are fairly heterogeneous, often due to the presence of dinucleotide repeats with varying numbers of the repeat, are analyzed in persons with and without a disease. It is most useful if rather large families can be found for this purpose. Studying sib pairs is also a useful technique but not quite so good as having large families to study. Commonly, the marker region of each individual family member is amplified by PCR and the amplified region is sequenced by DNA sequencing to determine the number of dinucleotide repeats in the individual. For example, a single heterogeneous marker may have anywhere from 18–23 dinucleotide repeats in the general population. For this example assume the relative frequencies are 5, 10, 15, 30, 30, 5 and 5% respectively for the 18, 19, 20, 21, 22 and 23 repeats. If the normal and affected individuals being tested show the same relative frequency of each type of repeat then it is unlikely that the marker is associated with the disease. However, if the affected population fairly consistently shows, e.g., only the 23 repeat version whereas the normal members of the family show the other repeats as well, there is a high likelihood that the marker is located near the gene causing the disease. In practice it is difficult to determine such an association unless the marker is located fairly close to the gene of interest. Crossing over of chromosomes leads to much of this complication. It is common to analyze many, many markers before any promising leads are found. Analyzing every individual in a family one by one is very laborious. It also can lead to complications such as in the case where, in an affected person, crossing over has occurred between the gene of interest and a marker which is relatively close to a gene of interest. In such a case it will appear that the marker is not located near the gene of interest. For a recessive gene in a person in which such a crossing over has occurred, such a person who has become hemizygous for the gene will have the recessive phenotype but will be seen as having a marker found in normal individuals rather than the marker found in affected individuals. This greatly confuses the data. A method to decrease such false results will be very useful.

The present invention decreases the complications introduced by crossing over between chromosomes. It does this by pooling the DNA of many individuals who are to be tested. This effectively decreases the background noise of the obtained data by summing the results seen for many affected individuals and prevents one from following up false positive results and therefore prevent a lot of unnecessary work going in the wrong direction. The present invention also uses a multiplexing or parallel processing technique by analyzing several markers, as many as 10–100, together in single lanes on a gel to speed up greatly the screening of markers to find those which are truly associated with the gene of interest. By combining these two pooling techniques and by using a method which does not require sequencing of individual marker regions but simply looks at the sizes of amplified products and the relative percentage of each size both in normal and in affected individuals, and then comparing these two sets of data via a simple difference spectrum, a very rapid screening of markers can be accomplished. This method results in an increase of 1 to 2 orders of magnitude compared to other methods which are presently used.

To perform the method of the invention, DNA is obtained from both normal and affected persons. The procedure gives better results as the number of individuals from whom DNA is obtained increases. It is also best to match the population of normal and affected persons as nearly as possible. Using blood relatives is the best approach if possible. Genetic markers to be tested are chosen. Primer pairs complementary to the genetic markers are made to be used in performing polymerase chain reactions. At least one of each primer pair is labeled with a marker, preferably a fluorescent marker. Two sets of primer pairs must be prepared, one of which has a first label and the other which has a second label. One set will be used to perform PCR with normal DNA as the template and the other set will be used to perform PCR with the affected (mutated) DNA as the template. The two labels must be distinguishable. Labels such as fluorescently labeled nucleotides which are commonly used for automated sequencing are preferred.

The DNA from the normal individuals will normally be pooled prior to performing PCR although the samples may be amplified individually. The DNA from the affected individuals is usually amplified individually rather than being pooled, although all of the individual affected DNA samples may be pooled prior to amplification. If this pooling is done prior to amplification some of the individual samples of DNA may be very underrepresented in the amplified DNA and not be seen. In performing the PCR on either the affected or normal DNA samples it is most preferable to perform individual reactions using only a single primer pair for each reaction and then pooling the PCR products. It is best to pool stoichiometric amounts of each amplified product. To reduce the number of reactions it is possible to pool primers in PCRs, e.g. using 3 primers pairs in a single reaction, but again this may result in underrepresentation of products from some primer pairs and data may be lost as a result. If this pooling of primer pairs is done, the primer pairs should be designed to have nearly identical $T_m$s.

After performing PCR, many samples are pooled and run together on a single lane of a sequencing gel. Ten to one hundred individual marker reactions may be mixed in a single lane. The amplified normal DNA and amplified affected DNA are mixed together to be run on the same lane. To measure the amplified products it is most preferable to scan the gel at the emission maxima of the two fluorescent labels. The intensity spectra of the two labels are recorded, normalized to one another and a difference spectrum is calculated. If none of the markers is associated with the disease of interest, the difference spectrum should be a nearly flat line. If one of the markers is associated with the disease, this marker will cause a peak in the difference spectrum. When a peak is observed it is necessary to redo the experiment using the pooled markers individually to determine which marker was responsible for the peak. Because it is rare to find a marker associated with a disease most experiments will not show a peak and the markers used in such experiments need not be tested individually. The ability to load as many as 100 markers into a single lane allows one to quickly screen and eliminate many markers. Further, by mixing markers in a single lane which give a wide range of sizes of amplified DNA, it is possible to narrow the choice of which markers gave a peak to only those markers producing amplified DNA of the size at which the peak occurred.

The present invention is described with reference to the following Examples, which are offered by way illustration and are not intended to limit the invention in any manner. Standard techniques well known in the art or the techniques specifically described below are utilized.

EXAMPLE 1

In this example, a single microsatellite maker is analyzed. It contains the dinucleotide marker $(CA)_n$ where n=10–15.

Primers corresponding to the unique DNA sequences on each side of the repeat region are used in a polymerase chain reaction to amplify the DNA from pools of individuals. The primers are selected such that an amplified DNA fragment is 60 bases in length when n=10 and 70 bases in length when n=15. DNA is isolated from 100 normal persons and pooled in stoichiometric amounts, and DNA is isolated from 10 affected blood relatives from the same family. This latter DNA may be pooled prior to amplification, but it is preferable to amplify the samples separately to assure no sample is underrepresented. If amplified separately, the amplified products are pooled prior to gel electrophoresis. The individuals chosen for the normal DNA samples are matched as closely as possible in genetic background to the affected individuals. Using members of the same family is the most preferable option. If this is not possible, then other factors are looked at. For example, if the affected population is African-American then the normal population should be African-American, if the affected population is Scandinavian then the normal population should be Scandinavian, etc. The two sets of DNA are each amplified by polymerase chain reactions. One primer used for the normal individuals is labeled with a blue fluorescent marker, and one primer used for the affected individuals is labeled with a red fluorescent marker. Following PCR, the two samples (normal and affected) are combined and electrophoresed in a single lane of a sequencing gel apparatus, for example the ABI Model 373. The amplified DNA sequences will vary from 60 bases in length up to 70 bases in length, with lengths of 60, 62, 64, 66, 68 and 70 bases being possible. As the samples are electrophoresed, the fluorescence emission is measured at the peak intensities of the two labels. The intensities are normalized to each other, and a difference spectrum is calculated. If the difference spectrum is a relatively flat line, this indicates that each of the two sets of amplified DNA have roughly the same percentage of each possible size of DNA products and no correlation between the marker and the disease is established. If the difference spectrum shows a marked peak in the difference spectrum, for example, at a size of 66 base pairs, this indicates that marker is closely associated with the disease under study. This results from the likely fact that the genetic mutation originated in a single ancestor who had the marker with 13 dinucleotide repeats which gives the 66 base amplified product. Thus all descendants who received the mutated gene will also receive the 66 base marker, unless of course there had been crossing over between the gene of interest and the marker. The closer the marker is to the gene of interest the cleaner will be the results. By pooling DNA from many individuals, such crossing over effects are diluted out.

EXAMPLE II

The first example just given was for a simple case of using only a single marker. The process of screening for a useful marker can be dramatically increased by using several markers simultaneously throughout all of the steps of the process. For this example, once again DNA is isolated from 100 blood relatives and pooled and DNA is isolated from 10 affected individuals from the same family and pooled. Here 3 sets of primer pairs will be utilized for PCR. It is preferable to choose markers and primers which will give a reasonable separation of DNA bands with minimal overlap when electrophoresed. Marker 1 may be a microsatellite region with a $(CA)_n$ repeat with n=10–13. Marker 2 may be similar with n=15–19, and marker 3 may have n=21–25. If each primer used is 15 nucleotides long, then marker 1 will give amplified DNA of sizes 50–56 base pairs, marker 2 will result in amplified DNA of 60–68 base pairs, and marker 3 will give sizes of 72–80 base pairs. In this scenario there is no overlap between any of the resulting products and the 3 markers can easily be distinguished on a single lane. As in Example I, the pooled DNAs are amplified via PCR except here the 3 sets of primers are used and all the resulting products are mixed together and electrophoresed in a single lane of a gel, the emission spectra are analyzed, and a difference spectrum is calculated. Again, a flat difference spectrum is indicative of a lack of correlation between the marker and the disease, whereas a peak in the difference spectrum indicates a correlation.

EXAMPLE III

This example will illustrate the simultaneous analysis of several markers for the situation in which the lengths of the amplified DNA fragments resulting from different marker regions overlap in size. Assume the case of 10 distinct markers, named A–J, each with $(CA)_n$ dinucleotide repeats. Further assume the case for which each marker is examined by performing PCR using primers which are all 15 nucleotides in length and immediately abut the $(CA)_n$ repeat region. Note that in practice the primers need not immediately abut the repeat region but can be moved farther away purposely to adjust the lengths of the amplified DNA fragments if such will be useful in achieving better separation of different markers. On sequencing gels, bands of DNA as large as 300 nucleotides can easily be distinguished from bands of DNA of length 301 nucleotides. Therefore primers may be moved quite some distance away from the repeat region to give products as large as approximately 300 nucleotides; there is no necessity of using only short products as in the 50–100 nucleotide length. This allows for running several samples together in a single lane and yet having minimal overlap between them. Lengths can also be adjusted somewhat by selection of the lengths of the primers used for the PCR. Table I lists the repeat size ranges and also the size ranges of the amplified products.

TABLE I

| Marker | Range of Repeats | Range of Lengths of Amplified Products |
| --- | --- | --- |
| A | 10–15 | 50–60 |
| B | 10–15 | 50–60 |
| C | 16–21 | 62–72 |
| D | 17–24 | 64–78 |
| E | 19–26 | 68–82 |
| F | 19–28 | 68–86 |
| G | 22–26 | 74–82 |
| H | 23–28 | 76–86 |
| I | 23–29 | 76–88 |
| J | 25–30 | 80–90 |

As in the previous example, two sets of reactions are performed, one in which stoichiometric amounts of DNA from 100 normal blood relatives are mixed for the PCR and one in which stoichiometric amounts of DNA from 10 affected blood relatives from the same family are used. One primer from each pair is labeled with either a blue fluorescent marker (for use with the normals) or a red fluorescent marker (for use with the affecteds). PCRs are performed using each set of primers in individual reactions. (Note: It may be possible to mix all the primers into a single PCR. If one desires to do this, balancing greater speed against the chance of missing a marker, it is best to choose primers which will all work equally well under a single set of PCR conditions, e.g., one will want to choose all sets of primers to have equal $T_m$s. Some minor variations between the primer efficiency is acceptable.) After performing the polymerase chain reactions the two sets of amplified DNA (that from the normals and the affecteds) is mixed and run on a sequencing gel apparatus. The emission spectra are recorded during the electrophoresis. The two spectra are then normalized and a difference spectrum is computed.

In this example it is seen that markers A and B will give amplified products which completely overlap in size range and do not overlap any of the other amplified products. Each marker appears in 6 different sizes in the normal population. Table II lists the percent of each size seen in the normals.

TABLE II

Expected % of Each Product in Normals

| Size of Amplified Product | % of Product for A | % of Product for B | % A + B |
| --- | --- | --- | --- |
| 50 | 5 | 10 | 7.5 |
| 52 | 10 | 10 | 10.0 |
| 54 | 20 | 30 | 25.0 |
| 56 | 50 | 25 | 37.5 |
| 58 | 5 | 10 | 7.5 |
| 60 | 10 | 15 | 12.5 |

When the amplified products are electrophoresed, if one looks solely at the blue spectrum produced from the normals in the range of 50–60 nucleotides and measures the area under the curve, one will see the relative percentages shown in the A+B column of Table II assuming that the amplification was equally efficient for the two sets of primers. If the amplifications were not equally efficient the values will change although this will not affect the ability to analyze the data unless the efficiencies were very different. For example, if A amplified 10 times as well as did B then marker B will be lost in the background and may not be seen. Such widely varying efficiencies are unexpected however. If neither A nor B is associated with the disease being studied in the affecteds, then the red spectrum shows the same relative percentages for each size band as for the normals. Note that this is true irrespective of the efficiencies of the amplifications. The one factor which will affect such a result will be the chance variation in the percentage of individuals with each size of marker. For example, assuming no association between the marker and the disease, it is expected that 50% of DNA samples from affected and unaffected persons will have an A marker of 56 nucleotides. If purely by chance only 30% of the affecteds had an A marker of 56 nucleotides then the difference spectrum will not result in a zero signal but will give a peak. The larger the number of samples which can be pooled, the smaller will be the chance of this purely random false positive result. The pooling of DNA samples from many individuals causes such peaks to diminish in size and to be lost in the background or to be recognized as purely random differences in the two populations.

If marker A is in fact associated with the disease and those with the disease all have an amplified marker A size of 54 nucleotides (assuming they have all received the mutated gene from a common ancestor and there has been no crossing over), there will be a dramatic difference spectrum seen. Assuming no association of marker B with the disease, the expected relative amount of each band in the affecteds is shown in Table III.

TABLE III

Expected % of Each Product in Affecteds for Which Marker A is Associated with the Disease and Marker B is not Associated with the Disease

| Size of Amplified Product | % of Product for A | % of Product for B | % A + B |
|---|---|---|---|
| 50 | 0 | 10 | 5 |
| 52 | 0 | 10 | 5 |
| 54 | 100 | 30 | 65 |
| 56 | 0 | 25 | 12.5 |
| 58 | 0 | 10 | 5 |
| 60 | 0 | 15 | 7.5 |

Calculating the difference spectrum of the results in Tables II and III using the data in the A+B column, one gets the results shown in Table IV.

TABLE IV

Difference Spectrum

| Fragment | Normal | Affected | Difference |
|---|---|---|---|
| 50 | 7.5 | 5 | 2.5 |
| 52 | 10.0 | 5 | 5.0 |
| 54 | 25.0 | 65 | -40 |
| 56 | 37.5 | 12.5 | 20 |
| 58 | 7.5 | 5 | 2.5 |
| 60 | 12.5 | 7.5 | 5.0 |

As seen in Table IV, the difference spectrum is dramatic. This difference is seen despite the fact that there was overlap in the experiment with a marker which is not associated with the disease. From such data it becomes obvious that either marker A or marker B is associated with the disease. It will be necessary to repeat the experiment using markers A and B separately to determine which is the one associated with the disease. Although it is necessary to repeat the experiment with the markers individually, in practice several hundred markers may be examined with none of them showing an association. In such an instance there will be no need to repeat the experiments using the markers individually. It is necessary to do so only in the rare instances in which a marker is actually found.

The example just given concerning markers A and B is for the relatively simple case in which only two markers overlap. As can be easily imagined or seen from the example shown in Table I, several markers could produce fragments which all overlap. For example, markers C, D, E and F will all produce amplified bands of 70 nucleotides. Nevertheless, a difference spectrum can still be observed although it will not be as dramatic as when only 1 or 2 markers are giving bands in a specific region. As noted earlier, it is best to use a mix of markers and primers which will give a wide spread to minimize the overlap. Adjusting the primer length can also be quite useful in spreading the bands. One trick along this line is to use primers which can shift the size of the amplified DNA fragment by a single base. In the examples above, it was stated that every primer was 15 nucleotides in length. The repeat involved was the simple dinucleotide CA. This results in products which all have an even number of base pairs. Instead of using primers only 15 nucleotides in length, for half of the markers use one primer which is 15 nucleotides in length and use as the other primer one which is 16 nucleotides in length. For these markers the resulting amplified products will all be of an odd number of base pairs and can easily be distinguished from those of an even number of base pairs. This trick doubles the number of markers which can effectively be used at a single time.

Many simple variations of the above methods can be easily imagined and these are considered to be within the scope of the present invention. Such variations include the labels used on the primers. A variety of different fluorescent colors may be chosen. One can even use radioactively labeled probes with two different radionuclides or use other nonfluorescent markers although such a method is much less convenient. Markers other than microsatellite regions of $(CA)_n$ repeats can of course be used. The number of markers used at one time and the number of samples of DNA which are pooled can be varied dramatically. The number of markers which are pooled must be balanced between two competing practicalities, one being that the more markers which are used together increases the rate of screening of markers but which must be balanced against the fact that as more markers are used and increasingly overlap the smaller will be the signal of a true positive result. In practice it is useful to use between 10–100 markers at a single time. The number of DNA samples which are pooled is important. The greater the number of samples used the better the averaging effect for the normals and the greater the summing effect for the affecteds.

What is claimed is:

1. A method to determine whether a tandem repeat DNA marker is associated with a disease of interest, said method comprising the steps of:

(a) preparing two sets of primer pairs for each of several tandem repeat markers, wherein each primer of a primer pair is complementary to sequence flanking a tandem repeat marker such that each pair of primers will amplify a tandem repeat marker in a polymerase chain reaction, wherein at least one primer of each pair from a first set of primer pairs is labeled with a first label and at least one primer of each pair from a second set of primer pairs is labeled with a second label wherein the said first label is distinguishable from said second label;

(b) purifying DNA from a population of normal persons to obtain normal DNA;

(c) purifying DNA from a population of persons affected with said disease to obtain affected DNA;

(d) performing polymerase chain reactions on said normal DNA using said first set of primer pairs to produce a first set of amplified DNA fragments and on said affected DNA using said second set of primer pairs to produce a second set of amplified DNA fragments;

(e) pooling said first set of amplified DNA fragments with said second set of amplified DNA fragments and separating the amplified fragments by electrophoresis on a gel;

(f) measuring a first signal resulting from said first label in said first set of amplified DNA fragments wherein said first signal indicates relative amounts of each size of amplified normal DNA fragments and measuring a second signal resulting from said second label in said second set of amplified DNA fragments wherein said second signal indicates relative amounts of each size of amplified affected DNA fragments;

(g) determining a difference spectrum between said first and second signals; and (h) examining said difference spectrum, wherein a difference spectrum showing a difference of close to zero throughout indicates no association of the tandem repeat markers with the disease and wherein a peak in the difference spectrum indicates an association of one or more tandem repeat markers with said disease;

wherein if an association is found, then steps (d) to (h) are repeated using each individual primer pair for each of said several tandem repeat markers from said first and second sets of primer pairs; and wherein tandem repeat markers amplified by said individual primer pairs which yield a peak in the difference spectrum are associated with said disease of interest.

2. The method of claim 1 wherein step (f) is performed during electrophoresis.

3. The method of claim 1 wherein step (f) is performed following electrophoresis.

4. The method of claim 1 wherein only one primer of each primer pair is labeled.

5. The method of claim 1 wherein both primers of each primer pair are labeled.

6. The method of claim 1 wherein the difference spectrum is determined by normalizing said first signal with said second signal to produce a scaled first signal and a scaled second signal and subtracting said scaled first signal from said scaled second signal.

7. The method of claim 1 wherein the normal DNA is pooled prior to performing polymerase chain reactions.

8. The method of claim 1 wherein said affected persons are blood relatives.

* * * * *